United States Patent [19]

Mengel et al.

[11] Patent Number: 4,655,824
[45] Date of Patent: * Apr. 7, 1987

[54] CERTAIN TRIFLUOROMETHOXY-PHENOXY-PYRIDINES HAVING HERBICIDAL ACTIVITY

[75] Inventors: Rudolf Mengel; Ludwig Schröder, both of Ingelheim; Werner Stransky, Gau-Algesheim; Gerbert Linden, Ingelheim; Sigmund Lust, Darmstadt, all of Fed. Rep. of Germany

[73] Assignee: Celamerck GmbH & Co. KG, Ingelheim am Rhein, Fed. Rep. of Germany

[*] Notice: The portion of the term of this patent subsequent to Jun. 12, 2001 has been disclaimed.

[21] Appl. No.: 620,120

[22] Filed: Jun. 13, 1984

Related U.S. Application Data

[63] Continuation of Ser. No. 462,150, Jan. 31, 1983, abandoned.

[30] Foreign Application Priority Data

Feb. 14, 1982 [DE] Fed. Rep. of Germany ....... 3205150

[51] Int. Cl.$^4$ ..................... C07D 213/64; A01N 43/40
[52] U.S. Cl. ......................................... 71/94; 546/295; 546/298; 546/302
[58] Field of Search ..................... 546/302, 298; 71/94

[56] References Cited

U.S. PATENT DOCUMENTS

| | | | |
|---|---|---|---|
| 3,429,689 | 2/1969 | Duerr et al. | 546/302 |
| 4,076,741 | 2/1978 | Bayer et al. | 260/465 F |
| 4,235,621 | 11/1980 | Nishiyama et al. | 546/302 |
| 4,317,913 | 3/1982 | Cartwright | 546/345 |
| 4,453,972 | 6/1984 | Schroder et al. | 71/94 |

Primary Examiner—Alan L. Rotman
Attorney, Agent, or Firm—Hammond & Littell, Weissenberger & Dippert

[57] ABSTRACT

Compounds of the formula

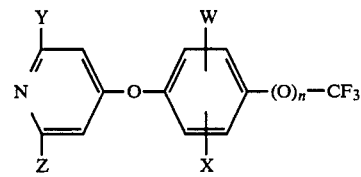

wherein

W and X, which may be identical to or different from each other, are each hydrogen, fluorine, chlorine, bromine, iodine, nitro, alkyl of 1 to 4 carbon atoms, fluoro-substituted alkyl of 1 to 4 carbon atoms or chloro-substituted alkyl of 1 to 4 carbon atoms;

Y is hydrogen, fluorine, chlorine, bromine, alkyl of 1 to 4 carbon atoms, fluoro-substituted alkyl of 1 to 4 carbon atoms or chloro-substituted alkyl of 1 to 4 carbon atoms;

Z is fluorine, chlorine, bromine, alkyl of 1 to 4 carbon atoms, fluoro-substituted alkyl of 1 to 4 carbon atoms, chloro-substituted alkyl of 1 to 4 carbon atoms, —COOH or —COO-(alkyl of 1 to 4 carbon atoms); and n is 0 or 1;

and, when Z is COOH, salts thereof, especially their alkali metal salts. The compounds as well as the salts are useful as selective herbicides.

7 Claims, No Drawings

CERTAIN TRIFLUOROMETHOXY-PHENOXY-PYRIDINES HAVING HERBICIDAL ACTIVITY

This is a continuation of copending application Ser. No. 462,150, filed Jan. 31, 193, now abandoned.

This invention relates to novel 4-phenoxy-substituted pyridines, to a method of preparing these compounds, to herbicidal compositions containing them as active ingredients, and to a method of using them as selective herbicides.

THE PRIOR ART

German Offenlegungsschrift No. 1,542,736 discloses herbicidal aryloxy-substituted pyridines of the formula

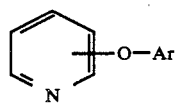

and particularly the compound of the formula

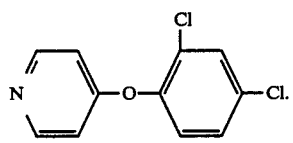

However, these compounds, which lack additional substituents on the pyridine ring, do not exhibit satisfactory herbicidal properties.

OBJECTS OF THE INVENTION

It is an object of the present invention to provide novel phenoxy-substituted pyridines having one or more additional substituents attached to the pyridine ring, which are more effective herbicides than the prior art compounds.

Other objects and advantages of the invention will become apparent as the description thereof proceeds.

DESCRIPTION OF THE INVENTION

More particularly, the present invention relates to a novel class of compounds represented by the formula

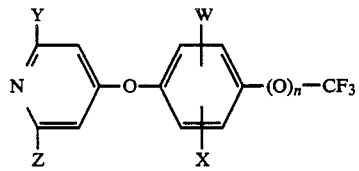

wherein
W and X, which may be identical to or different from each other, are each hydrogen, fluorine, chlorine, bromine, iodine, nitro, alkyl of 1 to 4 carbon atoms, fluoro-substituted alkyl of 1 to 4 carbon atoms or chloro-substituted alkyl of 1 4 carbon atoms;
Y is hydrogen, fluorine, chlorine, bromine, alkyl of 1 to 4 carbon atoms, fluoro-substituted alkyl of 1 to 4 carbon atoms or chloro-substituted alkyl of 1 to 4 carbon atoms;
Z is fluorine, chlorine, bromine, alkyl of 1 to 4 carbon atoms, fluoro-substituted alkyl of 1 to 4 carbon atoms, chloro-substituted alkyl of 1 to 4 carbon atoms, -COOH or -COO-(alkyl of 1 to 4 carbon atoms); and n is 0 or 1;

and, when Z is COOH, salts thereof, especially their alkali metal salts.

Those alkyl radicals in formula I which contain 3 or 4 carbon atoms may be straight-chain or branched-chain alkyls. Preferred fluoro-alkyls and chloro-alkyls are trifluoromethyl or trichloromethyl.

Preferred embodiments of variables W, X, Y, Z and n are the following
W: Hydrogen, chlorine, fluorine, methyl, trifluoromethyl and nitro;
X: Hydrogen, fluorine, chlorine, methyl, trifluoromethyl and nitro;
Y: Hydrogen, fluorine, chlorine, trifluoromethyl, trichloromethyl and methyl;
Z: Fluorine, chlorine, trifluoromethyl, methyl, carboxyl, methoxycarbonyl and ethoxycarbonyl; n: 0.

The compounds embraced by formula I may be prepared by a method involving known chemical synthesis principles, namely by reacting a pyridine derivative of the formula

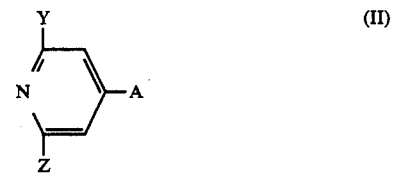

wherein
Y and X have the same meanings as in formula I, and
A is halogen, especially chlorine or fluorine, or nitro,
with a phenol of the formula

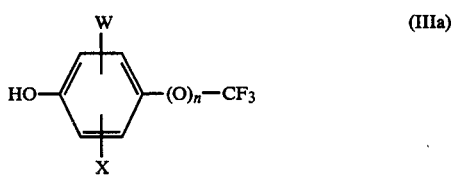

or with a phenolate of the formula

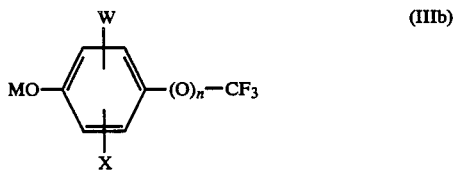

wherein
W, X and n have the same meanings as in formula I, and
M is one equivalent of a cation, preferably Na+, K+ or ½ Ca++.

The reaction is carried out at temperatures between ambient temperature and about 160° C., preferably in a polar solvent, such as acetone, butan-2-one, acetonitrile, dimethylformamide or dimethylsulfoxide, at room temperature or moderately elevated temperature. If the reaction is performed with a phenol of the formula IIIa, an acid-binding agent, for example an alkali metal carbonate, such as sodium carbonate or potassium carbonate, or an alkali metal or alkaline earth metal hydroxide such as sodium hydroxide, potassium hydroxide or calcium hydroxide, is added to the reaction mixture. In order to achieve a favorable yield, it can be of advantage to provide the phenol or phenolate and/or the acid-binding agent in excess.

The starting compounds of the formulas II, IIIa and IIIb are either known compounds or may be prepared by the same method as the known compounds.

The following examples illustrate the present invention and will enable others skilled in the art to understand it more completely. It should be understood, however, that the invention is not limited solely to the particular examples given below.

EXAMPLE 1

2,6-Dichloro-4-(2-chloro-4-trifluoromethyl-phenoxy)-pyridine 16.5 gm (0.12 mol) of potassium carbonate were added in portions to an ice-cooled and stirred suspension of 19.65 gm (0.1 mol) of 2-chloro-4-trifluoromethyl-phenol and 19.29 gm (0.1 mol) of 2,6-dichloro-4-nitro-pyridine. The resulting mixture was stirred for 2 hours at room temperature, and was then stirred into 250 ml of ice water. An oil separated out, which crystallized after some time. The crystalline product was collected by suction filtration, washed with water and dissolved in chloroform. The resulting solution was shaken with water, and the organic phase was separated, dried with sodium sulfate and evaporated to dryness. 25.3 gm (75% of theory) of the title compound were obtained as a colorless substance having a melting point of 66° C.

EXAMPLE 2

2-Chloro-6-methyl-4-(2-chloro-4-trifluoromethyl-phenoxy)-pyridine 16.5 gm (0.12 mol) of potassium carbonate were added in portions to a stirred solution of 19.65 gm (0.1 mol) of 2-chloro-4-trifluoromethyl-phenyl and 17.25 gm (0.1 mol) of 2-chloro-6-methyl-4-nitro-pyridine in 40 ml of dimethylformamide, and the mixture was heated to 80° C. and maintained at that temperature for 3 hours. Thereafter, the reaction mixture was allowed to cool and was then poured into 200 ml of ice water, and the aqueous mixture was extracted with chloroform. The organic phase was separated, washed with water, dried with sodium sulfate and evaporated. The residue was purified by column chromatography on silicagel, yielding a viscous oil which crystallized after some time. 20.9 gm (65% of theory) of the title compound, m.p. 75° C., were obtained.

Analysis: $C_{13}H_8Cl_2F_3NO$ (mol. wt. 322.11): Calc.: C-48.5%; H-2.5%; N-4.35%. Found: C-47.92%; H-2.27%; N-4.75%.

EXAMPLE 3

2-Chloro-4-(2-chloro-4-trifluoromethyl-phenoxy)-pyridine 2.48 gm (0.018 mol) of potassium carbonate were added in portions to a stirred solution of 2.95 gm (0.015 mol) of 2-chloro-4-trifluoromethyl-phenol and 2.2 gm (0.015 mol) of 2-chloro-4-nitro-pyridine in 10 ml of dimethylformamide, and the mixture was stirred first for 1 hour at room temperature and then for 1½ hours at 80° C. Thereafter, the reaction mixture was poured into ice water, and the aqueous mixture was extracted with chloroform. The organic phase was separated, washed with 2N sodium hydroxide and with water, dried with sodium sulfate and evaporated, yielding the title compound as a colorless oil.

Analysis: $C_{16}H_6Cl_2F_3NO$: Calc.: C-46.7%; H-1.96%; Cl-23.01%. Found C-46.03%; H-1.61%; Cl-22.67%.

1H-NMR (CDCl$_3$, ppm):

Protons in the pyridine moiety:1 proton at 8.22 ppm, 2 protons at 6.71 ppm.

Protons in the phenyl moiety: 1 proton each at 7.76, 7.56 and 7.22 ppm.

EXAMPLE 4

2 Chloro-6-methoxycarbonyl-4-(2 chloro-4-trifluoromethylphenoxy)-pyridine

A mixture consisting of 2.06 gm (0.01 mol) of methyl 4,6-dichloro-picolinate, 2.15 gm (0.011 mol) of chloro-4-trifluoromethyl-phenol, 1.5 gm of pulverized potassium carbonate and 5 ml of dimethylformamide was heated at 120° C. for one hour, while stirring. The mixture solidified. The solid mass was stirred and decanted several times with ice water, then acidified with acetic acid, and finally extracted with ethyl acetate. The organic phase was separated, washed with water and dried with sodium sulfate. The solvent was distilled off, and the residual oil was purified by chromatography on 40 gm of silicagel (eluant: Diisopropyl ether). 1.4 gm (38% of theory) of the title compound were obtained as a virtually colorless oil. $R_f$-value: 0.48 (prepared thin-layer chromatography plates manufactured by E. Merck, Darmstadt, Germany, with silicagel 60-F-254 Eluant: Acetone/diisopropyl ether 1:2; the spots are visible in ultraviolet light at 254 μm).

The prepared thin-layer chromatography plates of the type used in this example and the ultra-violet light of the indicated wavelength were also used for the determination of the $R_f$-values in the subsequent examples.

The following tables I–VI show compounds of the formula I which were prepared in analogy to Examples 1–4.

TABLE I

| Example | Y | Z | Remarks |
|---|---|---|---|
| 5 | —H | —CH$_3$ | |
| 6 | —CH$_3$ | —CH$_3$ | |
| 7 | —H | —CF$_3$ | |
| 8 | —H | —F | |
| 9 | —F | —F | b.p. 112–114° C./0.05 mbar |
| 10 | —Cl | —CF$_3$ | |
| 11 | —F | —CH$_3$ | |
| 12 | —Cl | —CCl$_3$ | |
| 13 | —F | —CCl$_3$ | |
| 14 | —H | —Br | |
| 15 | —Br | —Br | |
| 16 | —CH$_3$ | —Br | |
| 17 | —CCl$_3$ | —Br | |
| 18 | —Br | —CF$_3$ | |
| 19 | —H | —OCH$_3$ | |
| 20 | —Cl | —OCH$_3$ | |
| 21 | —H | —O—n-C$_4$H$_9$ | |
| 22 | —H | —COOH | |
| 23 | —H | —COOC$_2$H$_5$ | |

TABLE I-continued

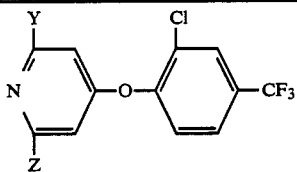

| Example | Y | Z | Remarks |
|---|---|---|---|
| 24 | —Cl | —COONa | |

TABLE II

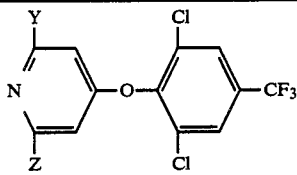

| Example | Y | Z | Remarks |
|---|---|---|---|
| 25 | —H | —CH$_3$ | |
| 26 | —CH$_3$ | —CH$_3$ | |
| 27 | —H | —CF$_3$ | |
| 28 | —H | —F | |
| 29 | —F | —F | |
| 30 | —Cl | —CF$_3$ | |
| 31 | —F | —CH$_3$ | |
| 32 | —Cl | —CCl$_3$ | |
| 33 | —F | —CCl$_3$ | |
| 34 | —H | —Br | |
| 35 | —Br | —Br | |
| 36 | —CH$_3$ | —Br | |
| 37 | —CCl$_3$ | —Br | |
| 38 | —Br | —CF$_3$ | |
| 39 | —H | —OCH$_3$ | |
| 40 | —Cl | —OCH$_3$ | |
| 41 | —H | —O—n-C$_4$H$_9$ | |
| 42 | —H | —CH(CH$_3$)$_2$ | |
| 43 | —H | —COOK | |
| 44 | —Cl | —Cl | oil, R$_f$-value 0.58[1] |
| 45 | —Cl | —COOCH$_3$ | |

[1]Eluant: Diisopropyl ether/gasoline 1:1

TABLE III

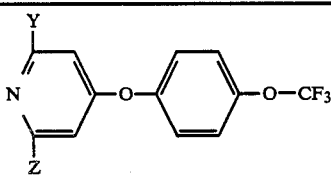

| Example | Y | Z | Remarks |
|---|---|---|---|
| 46 | —H | —CH$_3$ | |
| 47 | —CH$_3$ | —CH$_3$ | |
| 48 | —H | —CF$_3$ | |
| 49 | —H | —F | |
| 50 | —F | —F | |
| 51 | —Cl | —CF$_3$ | |
| 52 | —F | —CH$_3$ | |
| 53 | —Cl | —Cl | oil, R$_f$-value 0.64[1] |
| 54 | —F | —CCl$_3$ | |
| 55 | —H | —Br | |
| 56 | —Br | —Br | |
| 57 | —CH$_3$ | —Br | |
| 58 | —CCl$_3$ | —Br | |
| 59 | —Br | —CF$_3$ | |
| 60 | —H | —OCH$_3$ | |
| 61 | —Cl | —OCH$_3$ | |
| 62 | —H | —O—n-C$_4$H$_9$ | |
| 63 | —C$_2$H$_5$ | —C$_2$H$_5$ | |
| 64 | —H | —C(CH$_3$)$_3$ | |
| 65 | —H | —COOH | |

TABLE III-continued

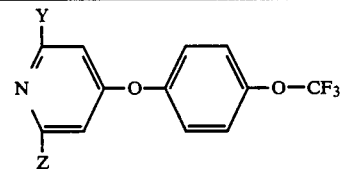

| Example | Y | Z | Remarks |
|---|---|---|---|
| 66 | —Cl | —CH$_3$ | oil, R$_f$-value 0.52[2] |
| 67 | —H | —Cl | oil, R$_f$-value 0.54[1] |

[1]Eluant: Diisopropyl ether/acetone 5:1
[2]Eluant: Diisopropyl ether

TABLE IV

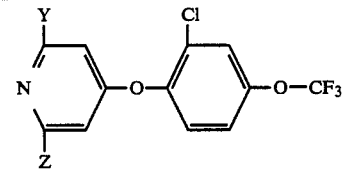

| Example | Y | Z | Remarks |
|---|---|---|---|
| 68 | —H | —CH$_3$ | |
| 69 | —CH$_3$ | —CH$_3$ | |
| 70 | —H | —CF$_3$ | |
| 71 | —H | —F | |
| 72 | —F | —F | |
| 73 | —Cl | —CF$_3$ | |
| 74 | —F | —CH$_3$ | |
| 75 | —Cl | —CCl$_3$ | |
| 76 | —F | —CCl$_3$ | |
| 77 | —H | —Br | |
| 78 | —Br | —Br | |
| 79 | —CH$_3$ | —Cl | m.p. 90° C. |
| 80 | —CCl$_3$ | —Br | |
| 81 | —Br | —CF$_3$ | |
| 82 | —H | —OCH$_3$ | |
| 83 | —Cl | —OCH$_3$ | |
| 84 | —H | —O—n-C$_4$H$_9$ | |
| 85 | —H | —CH(CH$_3$)$_2$ | |
| 86 | —H | —COOH | |
| 87 | —H | —COOC$_2$H$_5$ | |
| 88 | —Cl | —Cl | m.p. 92° C. |

TABLE V

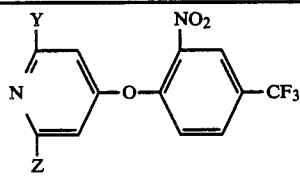

| Example No. | Y | Z | Remarks |
|---|---|---|---|
| 89 | —H | —CH$_3$ | |
| 90 | —CH$_3$ | —CH$_3$ | |
| 91 | —H | —CF$_3$ | |
| 92 | —H | —F | |
| 93 | —F | —F | |
| 94 | —Cl | —CF$_3$ | |
| 95 | —F | —CH$_3$ | |
| 96 | —Cl | —CCl$_3$ | |
| 97 | —F | —CCl$_3$ | |
| 98 | —H | —Br | |
| 99 | —Br | —Br | |
| 100 | —CH$_3$ | —Br | |
| 101 | —CCl$_3$ | —Br | |
| 102 | —Br | —CF$_3$ | |
| 103 | —H | —OCH$_3$ | |
| 104 | —Cl | —OCH$_3$ | |
| 105 | —H | —O—n-C$_4$H$_9$ | |

TABLE V-continued

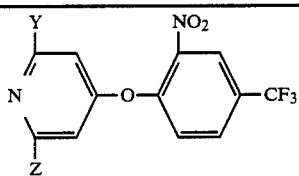

| Example No. | Y | Z | Remarks |
|---|---|---|---|
| 106 | —Cl | —Cl | m.p. 113–115° C. |
| 107 | —CH₃ | —Cl | |
| 108 | —H | —COOH | |
| 109 | —Cl | —COOCH₃ | |

TABLE VI

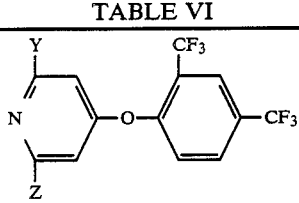

| Example No. | Y | Z |
|---|---|---|
| 110 | —H | —CH₃ |
| 111 | —CH₃ | —CH₃ |
| 112 | —H | —CF₃ |
| 113 | —H | —F |
| 114 | —F | —F |
| 115 | —Cl | —CF₃ |
| 116 | —F | —CH₃ |
| 117 | —Cl | —CCl₃ |
| 118 | —F | —CCl₃ |
| 119 | —H | —Br |
| 120 | —Br | —Br |
| 121 | —CH₃ | —Br |
| 122 | —CCl₃ | —Br |
| 123 | —Br | —CF₃ |
| 124 | —H | —OCH₃ |
| 125 | —Cl | —OCH₃ |
| 126 | —H | —O—n-C₄H₉ |
| 127 | —H | —n-C₃H₇ |
| 128 | —H | —n-C₄H₉ |
| 129 | —F | —C₂H₅ |
| 130 | —H | —COOH |

The compounds of the present invention, that is, those embraced by formula I above and, when Z is —COOH, theirs salts, especially their alkali metal salts, have useful properties. More particularly, they exhibit biocidal, expecially herbicidal activity Unlike the prior art compounds above referred to, the compounds of the present invention are very effective herbicides, against numerous monocotyl and dicotyl weeds, including such difficultly combatable weeds as *Galium aparine* and *Veronica hederifolia*.

An especially valuable point is that various important gaps in the range of activities of a number of otherwise very useful products can be filled by using these products in conjunction with the novel compounds of this invention. Examples of partners for combined use in this way include chlortoluron and related urea derivatives, terbutryn and related triazine derivatives, trifluralin and related derivatives, alachlor, dimethachlor and related compounds.

The herbicidal activity of the novel compounds was tested in a greenhouse test using a quantity of 2 kg/ha (pre-emergence values). The comparison substance used was A =4-(2,4-dichloro-phenoxy)-pyridine according to German Offenlegungsschrift No. 15 42 736.

The results were evaluated on the nine-point evaluation scale, where 1=100% activity and 9=no activity.

| Compound | SIN* | LYC* | ECH* |
|---|---|---|---|
| A (prior art) | 9 | 9 | 9 |
| According to the invention | | | |
| Example 1 | 1 | 1 | 1 |
| Example 2 | 1 | 1 | 1 |

*SIN = *Sinapis alba*
*LYC = *Lycopersicum esculentum*
*ECH = *Echinocloa crus galli*

The novel compounds not only have a good weed killing activity, but are also well tolerated by numerous useful crops such as oats, wheat, barley, potatoes, soybeans, cotton and peas, thus permitting selective use.

The compounds may be applied both pre- and postemergence. If the new active substances are used by themselves, they are preferably applied pre-emergence. If they are to be used in combination, especially for postemergence treatment, the following particularly suitable partners:

1. Growth-active herbicides, such as 2,4-DP, MCPA, CMPP;
2. Contact herbicides such as ioxynil, bromoxynil, bentazone, bromophenoxime, dinoterb;
3. Grass herbicides such as isoproturon and diclofop-methyl.

For herbicidal purposes the compounds of the present invention are incorporated as active ingredients into conventional herbicidal compositions, such as solutions, dusting powders, wettable powders, emulsion concentrates and the like, consisting essentially of inert ingredients, such as carriers, dispersants, emulsifiers, wetting agents and the like, and an effective herbicidal amount of a compound of the present invention.

For weed control the compounds of the present invention are applied to the weed-infested area at the rate of about 0.05 to 2 kg, preferably 0.1 to 1 kg, per hectare, depending on the particular compound which is used and the weed to be controlled. When they are used in conjunction with other herbicides, even smaller quantities (down to about 0.03 kg/ha) of the compounds according to the invention are generally used.

The following examples illustrate a few herbicial compositions comprising a compound of the present invention as an active ingredient and represent the best modes contemplated of using the invention. The percentages in these examples are percent by weight.

EXAMPLE 131

Wettable Powder 1

25% active ingredient of the formula I
55% kaolin
9% lignin sulfonate as dispersant
1% sodium tetrapropylenebenzene sulfonate as wetting agent.

EXAMPLE 132

Wettable powder 2

80% active ingredient of the formula I
8% calcium lignin sulfonate
5% colloidal silicic acid
5% sodium sulfate
2% sodium disobutyl naphthalene sulfonate.

EXAMPLE 133

Emulsion Concentrate

40% active ingredient of the formula I
25% Shellsol A (liquid mixture of aromatic hydrocarbon)
25% N-methyl-pyrrolidone
10% Emulsogen I 40 (anionic emulsifier)

Prior to use, the compositions of Examples 131 to 133 are diluted with water to an active ingredient content of 0.05 to 5% by weight.

While the present invention has been illustrated with the aid of certain specific embodiments thereof, it will readily be apparent to others skilled in the art that the invention is not limited to these particular embodiments, and that various changes and modifications may be made without departing from the spirit of the invention or the scope of the appended claims.

We claim:

1. A compound of the formula

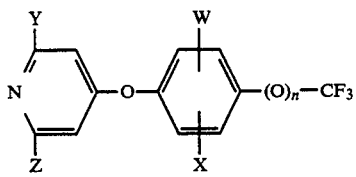

(I)

wherein

W and X are each hydrogen, fluorine, chlorine, bromine, iodine, nitro, alkyl of 1 to 4 carbon atoms, fluoro-substituted alkyl of 1 to 4 carbon atoms or chloro-substituted alkyl of 1 to 4 carbon atoms;

Y is hydrogen, fluorine, chlorine, bromine, alkyl of 1 to 4 carbon atoms, fluoro-substituted alkyl of 1 to 4 carbon atoms or chloro-substituted alkyl of 1 to 4 carbon atoms;

Z is fluorine, chlorine, bromine, alkyl of 1 to 4 carbon atoms, fluoro-substituted alkyl of 1 to 4 carbon atoms, chloro-substituted alkyl of 1 to 4 carbon atoms, —COOH or —COO—(alkyl of 1 to 4 carbon atoms); and n is 1;

or, when Z is —COOH, an alkali or alkaline earth metal salt thereof.

2. A compound of claim 1,
where
W and X are each hydrogen, fluorine, chlorine, methyl, trifluoromethyl or nitro;
Y is hydrogen, fluorine, chlorine, methyl, trifluoromethyl or trichloromethyl;
Z is fluorine, chlorine, methyl, trifluoromethyl or carboxyl; and
n is 1;

or, when Z is carboxyl, an alkali or alkaline earth metal salt thereof.

3. A compound of claim 1, where said salt is an alkali metal salt.

4. A compound of claim 2, where said salt is an alkali metal salt.

5. An herbicidal composition consisting essentially of an effective herbicidal amount of a compound of claim 1 in combination with an inert carrier.

6. The method of killing weeds, which comprises contacting said weeds with an effective herbicidal amount of a composition of claim 5.

7. The method of killing weeds, which comprises contacting said weeds with an effective herbicidal amount of a compound of claim 1.

* * * * *

UNITED STATES PATENT AND TRADEMARK OFFICE
CERTIFICATE OF CORRECTION

PATENT NO. : 4,655,824

DATED : April 7, 1987

INVENTOR(S) : RUDOLF MENGEL ET AL.

It is certified that error appears in the above-identified patent and that said Letters Patent is hereby corrected as shown below:

Column 1, line 7: "193," should read -- 1983, --.

Column 1, line 61: "14" should read -- 1 to 4 --.

Column 4, line 15: "2 Chloro" should read -- 2-Chloro --.

Column 4, line 19: "chloro-4-" should read -- 2-chloro-4- --.

Column 8, line 22: "following particularly" should read -- following are particularly --.

Signed and Sealed this

Twenty-second Day of September, 1987

Attest:

DONALD J. QUIGG

Attesting Officer     Commissioner of Patents and Trademarks